(12) United States Patent
Pacetti

(10) Patent No.: US 8,282,024 B2
(45) Date of Patent: Oct. 9, 2012

(54) STENT COATING NOZZLE ASSEMBLY

(75) Inventor: Stephen Dirk Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 491 days.

(21) Appl. No.: 12/027,077

(22) Filed: Feb. 6, 2008

(65) Prior Publication Data

US 2008/0121175 A1    May 29, 2008

Related U.S. Application Data

(62) Division of application No. 10/606,712, filed on Jun. 26, 2003, now Pat. No. 7,341,630.

(51) Int. Cl.
*B05B 7/06* (2006.01)

(52) U.S. Cl. ....... 239/428; 239/296; 239/290; 427/2.25; 118/500

(58) Field of Classification Search .................. 239/428, 239/296, 290; 118/300, 303, 500; 427/2.25
See application file for complete search history.

(56) References Cited

U.S. PATENT DOCUMENTS

| | | | |
|---|---|---|---|
| 2,373,595 A | 4/1945 | Peeps | |
| 3,049,439 A | 8/1962 | Coffman | |
| 3,232,540 A | 2/1966 | Cassanmangnago | |
| 3,848,807 A * | 11/1974 | Partida | 239/290 |
| 4,733,665 A | 3/1988 | Palmaz | |
| 4,743,252 A | 5/1988 | Martin et al. | |
| 4,800,882 A | 1/1989 | Gianturco | |
| 4,886,062 A | 12/1989 | Wiktor | |
| 4,967,606 A | 11/1990 | Wells et al. | |
| 5,015,505 A | 5/1991 | Cetnar | |
| 5,075,138 A * | 12/1991 | Tanaka et al. | 427/213 |
| 5,225,750 A | 7/1993 | Higuchi et al. | |
| 5,249,746 A | 10/1993 | Kaneko et al. | |
| 5,368,560 A | 11/1994 | Rambo et al. | |
| 5,435,491 A * | 7/1995 | Sakuma | 239/296 |
| 5,437,889 A | 8/1995 | Jones | |
| 5,447,567 A * | 9/1995 | Tanaka et al. | 118/303 |
| 5,464,650 A | 11/1995 | Berg et al. | |
| 5,511,726 A | 4/1996 | Greenspan et al. | |
| 5,527,337 A | 6/1996 | Stack et al. | |

(Continued)

FOREIGN PATENT DOCUMENTS

JP 2003211063 7/2003

(Continued)

OTHER PUBLICATIONS

English Translated Abstract of JP 2003211063A.

(Continued)

*Primary Examiner* — Len Tran
*Assistant Examiner* — Trevor E McGraw
(74) *Attorney, Agent, or Firm* — Squire Sanders (US) LLP

(57) ABSTRACT

A system, nozzle assembly, and method for coating a stent with a solvent and polymer are provided. The polymer can include a therapeutic substance or a drug. The polymer and solvent can be discharged from separate tubes disposed within another tube carrying moving air. The polymer and the solvent mix together when they are discharged and are atomized by the air. The ends of the tubes can be concentric with each other. The ends of the tubes can also be positioned relative to each other to prevent accumulation of polymer at the ends of the tubes.

11 Claims, 5 Drawing Sheets

U.S. PATENT DOCUMENTS

| | | | | |
|---|---|---|---|---|
| 5,662,922 A | * | 9/1997 | Christensen | 424/438 |
| 5,687,906 A | * | 11/1997 | Nakagawa | 239/8 |
| 5,700,286 A | | 12/1997 | Tartaglia et al. | |
| 5,713,949 A | | 2/1998 | Jayaraman | |
| 5,741,554 A | | 4/1998 | Tisone | |
| 5,766,710 A | | 6/1998 | Turnlund et al. | |
| 5,769,883 A | | 6/1998 | Buscemi et al. | |
| 5,810,254 A | | 9/1998 | Kropfield | |
| 5,824,056 A | | 10/1998 | Rosenberg | |
| 5,837,313 A | | 11/1998 | Ding et al. | |
| 5,843,172 A | | 12/1998 | Yan | |
| 5,869,127 A | | 2/1999 | Zhong | |
| 5,873,904 A | | 2/1999 | Ragheb et al. | |
| 5,957,899 A | * | 9/1999 | Spears et al. | 604/264 |
| 5,980,972 A | | 11/1999 | Ding | |
| 5,984,449 A | | 11/1999 | Tajika et al. | |
| 6,056,993 A | * | 5/2000 | Leidner et al. | 427/2.25 |
| 6,068,202 A | * | 5/2000 | Hynes et al. | 239/290 |
| 6,096,070 A | | 8/2000 | Ragheb et al. | |
| 6,121,027 A | | 9/2000 | Clapper et al. | |
| 6,132,809 A | | 10/2000 | Hynes et al. | |
| 6,143,370 A | | 11/2000 | Panagiotou et al. | |
| 6,203,551 B1 | * | 3/2001 | Wu | 606/108 |
| 6,209,621 B1 | | 4/2001 | Treacy | |
| 6,214,407 B1 | | 4/2001 | Laube et al. | |
| 6,224,675 B1 | | 5/2001 | Prentice et al. | |
| 6,395,326 B1 | | 5/2002 | Castro et al. | |
| 6,462,284 B1 | | 10/2002 | Hashimoto | |
| 6,491,666 B1 | | 12/2002 | Santini, Jr. et al. | |
| 6,503,954 B1 | | 1/2003 | Bhat et al. | |
| 6,562,136 B1 | * | 5/2003 | Chappa et al. | 118/500 |
| 6,723,373 B1 | * | 4/2004 | Narayanan et al. | 427/2.25 |
| 6,767,637 B2 | | 7/2004 | Park et al. | |
| 6,969,012 B2 | | 11/2005 | Kangas et al. | |
| 6,972,054 B2 | * | 12/2005 | Kerrigan | 118/500 |
| 7,338,557 B1 | * | 3/2008 | Chen et al. | 118/500 |
| 7,341,630 B1 | * | 3/2008 | Pacetti | 118/300 |
| 7,345,480 B2 | * | 3/2008 | Pai et al. | 324/309 |
| 7,354,480 B1 | * | 4/2008 | Kokish et al. | 118/500 |
| 7,390,523 B2 | * | 6/2008 | Pacetti et al. | 427/2.24 |
| 2003/0099765 A1 | | 5/2003 | Jayaraman | |
| 2003/0143315 A1 | | 7/2003 | Pui et al. | |
| 2003/0196595 A1 | * | 10/2003 | Takeshita et al. | 118/58 |
| 2003/0215564 A1 | * | 11/2003 | Heller et al. | 427/2.25 |
| 2003/0225365 A1 | * | 12/2003 | Greff et al. | 604/43 |
| 2003/0225391 A1 | * | 12/2003 | Cragg et al. | 604/508 |
| 2005/0202156 A1 | * | 9/2005 | O'Connor et al. | 427/2.1 |
| 2006/0038027 A1 | * | 2/2006 | O'Connor et al. | 239/8 |

FOREIGN PATENT DOCUMENTS

| | | |
|---|---|---|
| WO | WO 98/23228 | 6/1998 |

OTHER PUBLICATIONS

"Impulse Jetting: About Us," http://www.impulsejetting.com/about.html, printed Dec. 18, 2000 (1 page).

"Impulse Jetting: Our Technology," http://www.impulsjetting.com/tech1.html, printedDec. 18, 2000 (1 page).

Trident, Inc., http://www.tridetintl.com/subbody.html, printed Sep. 18, 2003 (1 page).

World Precision Instruments, Inc., "Nanolite Injector," http://www.wpiinc.com/WPI_Web/Microinjection/Nanoliter_Injector.html, printed Sep. 18, 2003 (2 pages).

World Precision Instruments, Inc., "Pneumatic PicoPumps," httm://www.wpi-europe.com/pumps/Pneumatic_PicoPumps.html, printed Sep. 18, 2003 (5 pages).

World Precision Instruments, Inc., "Nanoliter 2000," http://www.wpi-europe.com/pumps/Nanoliter_Injector.html, printed Sep. 18, 2003 (3 pages).

World Precision Instruments, Inc., http://www.wpiinc.com/WPI_Web/Pumps/pneumatic_Fig.gif, printed Sep. 30, 2002 (1 page).

World Precision Instruments, Inc., "Pneumatic PicoPumps," http://www.wpiinc.com/WPI_Web/Microinjection/Pneumatic_PicoPumps.html, printed Sep. 18, 2003 (4 pages).

* cited by examiner

STENT COATING NOZZLE ASSEMBLY

This application is a divisional application of U.S. application Ser. No. 10/606,712, filed Jun. 26, 2003 now U.S. Pat. No. 7,341,630, which is incorporated herein by reference in its entirety.

TECHNICAL FIELD

This invention relates to a nozzle assembly used in the process of coating a stent, and more particularly provides a nozzle for use in drug eluting stent spray coating.

BACKGROUND

Blood vessel occlusions are commonly treated by mechanically enhancing blood flow in the affected vessels, such as by employing a stent. Stents act as scaffolding, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by spraying the composition onto the stent. The solvent is allowed to evaporate, leaving on the stent surfaces a coating of the polymer and the therapeutic substance impregnated in the polymer.

However, a shortcoming of the above-described method of medicating a stent is the potential for clogging of a spray nozzle used to the coat the stent. The clogging is caused by accumulation of solid polymer on and around the nozzle tip from which the polymer solution exits. The clogging can lead to a drift in the flow rate, which in turn leads to a variation in total drug content from stent to stent, a variation in the drug release rate from stent to stent, and non-uniform coating of the stents.

Accordingly, a new nozzle for spraying coating is needed to minimize nozzle blockage and the associated variability in the coating behavior.

SUMMARY

Briefly and in general terms, the present invention is directed to a nozzle assembly to dispose a solvent and a polymer onto a stent. In aspects of the present invention, the assembly comprises a first tube to deliver a composition including a polymer to a stent, a second tube disposed over the first tube to deliver a solvent completely or significantly free from any drugs or the polymer, the solvent adapted to blend or mix with the composition when the composition and the solvent are discharged out from the first tube and the second tube, respectively, and a third tube disposed over the second tube to atomize the composition and the solvent that are applied to the stent. In detailed aspects, the nozzle assembly enables external atomization and mixing of the solvent and polymer. In other detailed aspects, the composition further includes a drug.

In other aspects of the present invention, the assembly comprises a first tube, a second tube, and a third tube. The first tubes has a first aperture, carries a composition including a polymer, and discharges the composition out of the first aperture. The second tube has a second aperture, carries a solvent completely or significantly free from drugs or the polymer, and discharges the solvent out of the second aperture. The second aperture, in further aspects, is positioned adjacent the first aperture such that the discharged solvent blends or mixes with the discharged composition. The third tube has a third aperture, carries a gas, and discharges the gas out of the third aperture. The third aperture, in further aspects, has an annular shape that surrounds an end segment of the first tube and an end segment of the second tube such that the discharged composition and the discharged solvent are atomized by the discharged gas.

The features and advantages of the invention will be more readily understood from the following detailed description which should be read in conjunction with the accompanying drawings.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

Figure 1:
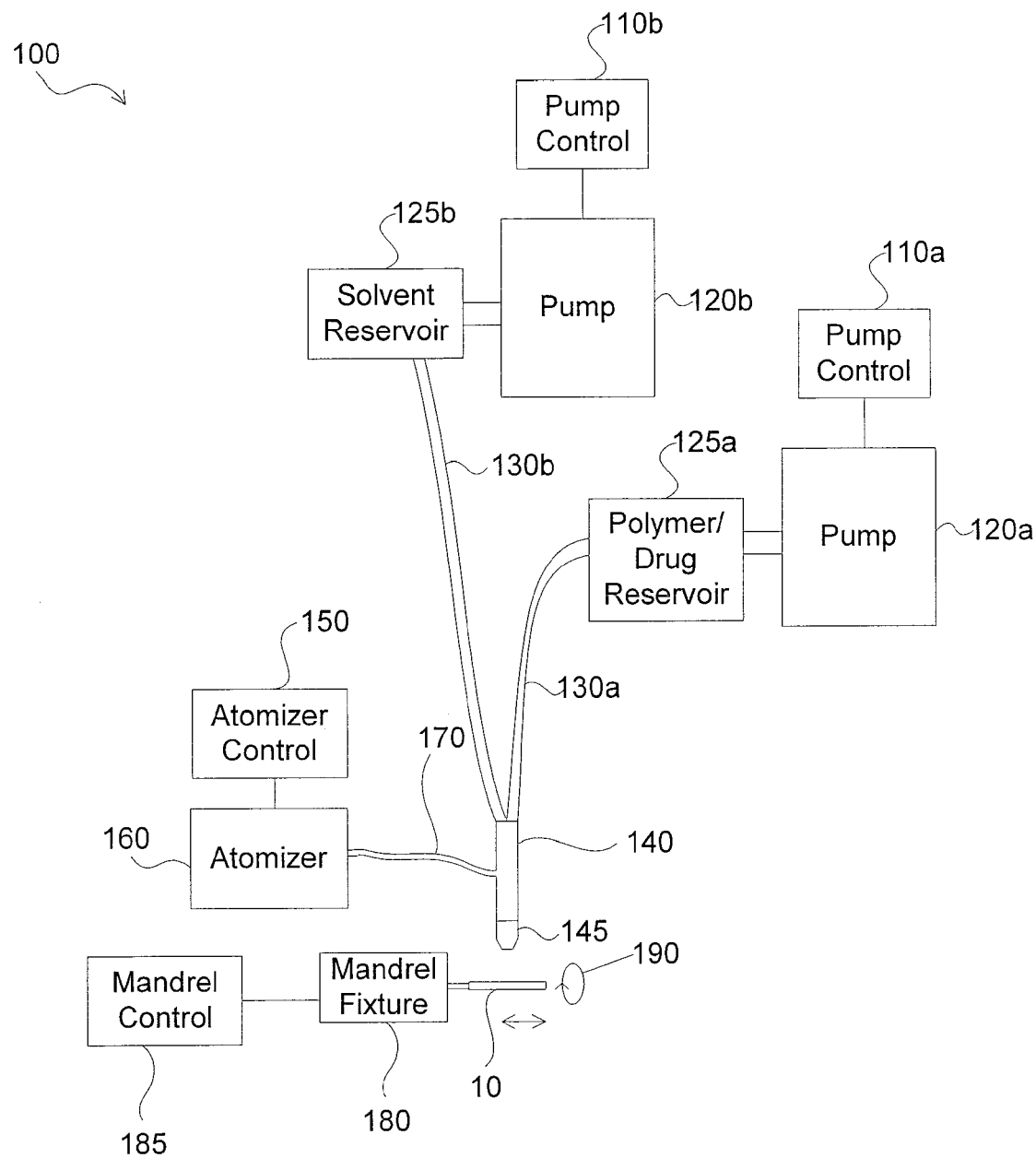
FIG. 1 is a block diagram illustrating a coating system for coating a stent with a composition.

FIG. 1 is a block diagram illustrating a coating system 100 for coating a stent 10 with a composition. The coating system 100 comprises pump controls 110a and 110b; pumps 120a and 120b; a polymer and/or drug reservoir 125a (referred to hereinafter as polymer/drug reservoir 125a), which may optionally include solvent(s) (for placing polymer and/or drug in a liquid composition form); a solvent reservoir 125b; a nozzle assembly 140 having a nozzle tip 145; an atomizer control 150; an atomizer 160; a mandrel fixture 180; and a mandrel fixture control 185. The pump control 110a is communicatively coupled to the pump 120a and controls the amount of polymer and/or drug dispensed by the pump 120a from the polymer/drug reservoir 125a. The pump control 110a may include mechanical and/or electrical control mechanisms. In an embodiment of the invention, the pump control 110a is integrated with the pump 120a. Similarly, the pump control 110b is communicatively coupled to the pump 120b and controls the amount of solvent dispensed by the pump 120b from the solvent reservoir 125b. The pump control 110b may include mechanical and/or electrical control mechanisms. In an embodiment of the invention, the pump control 110b is integrated with the pump 120b. In another embodiment of the invention, the pump controls 110a and 110b are combined into a single unit that controls the pumps 120a and 120b.

The pumps 120a and 120b pump a polymer/drug combination and a solvent from the reservoirs 125a and 125b respectively, for coating the stent 10 in situ, to the nozzle assembly 140 via a tubing 130a and 130b respectively. The pumps 120a and 120b may pump the contents of the reservoirs 125a and 125b at a rate of 0.15 cc/min, for example. In an embodiment of the invention, the pumps 120a and 120b can pump the contents of the reservoirs 125a and 125b, respectively, at different rates. Further, the pump 120b may alone pump solvent so as to clean the nozzle 140. In one embodiment of the invention, the pumps 120a and 120b include a syringe pumps. In another embodiment of the invention, the pumps 120a and 120b include a gear pumps. It will be appreciated that the pumps 120a and 120b can comprise other types of pumps and/or combinations of pumps such as positive displacement pumps, constant displacement pumps or green pumps.

Representative examples of polymers that can be used to coat a stent include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(glycerolsebacate); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly (ether esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride, poly(vinylidene fluoride-co-hexafluoropropene), and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and/or the therapeutic substance and is capable of dissolving the polymer and/or therapeutic substance at the concentration desired. The solvent in the solvent reservoir 125b could be, in one embodiment, an excellent solvent for the polymer but a poor solvent for the therapeutic substance. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and mixtures and combinations thereof.

The therapeutic substance or drug can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, dexamethasone, and rapamycin.

The atomizer 160 supplies high-pressure air to the nozzle assembly 140 via a tubing 170. This high-pressure air is used to atomize the polymer/drug composition and the solvent dispensed from the nozzle assembly 140 onto the stent 10, as will be discussed in further detail below. The atomizer control 150 is communicatively coupled to the atomizer 160 and controls the pressure of the air dispensed from the atomizer 160 to the nozzle assembly 140. The atomizer control 150 can include electrical mechanisms, mechanical mechanisms, or a combination thereof to control the atomizer 160. In an embodiment of the invention, the atomizer control 150 and the atomizer 160 can be integrated into a single device. In another embodiment of the invention, the atomizer 160 can include an ultrasonic atomizer that uses ultrasound in place of atomizing air to atomize the polymer/drug composition and the solvent.

The mandrel fixture 180 supports the stent 10 during a coating application process. In addition, the mandrel fixture 180 can include an engine so as to provide rotational motion about the longitudinal axis of the stent 10, as depicted by the arrow 190, during the coating process. Another motor can also be provided for moving the stent 10 in a linear direction, back and forth. The mandrel control 185 is communicatively coupled to the mandrel fixture 180 and controls movement of the stent 10. The type of stent that can be crimped on the mandrel fixture 180 is not of critical significance. The term stent is broadly intended to include self- and balloon-type expandable stents as well as stent-grafts. It will be appreciated by one of ordinary skill in the art that other implantable devices can be used in place of stents.

The nozzle assembly 140, as will be discussed in further detail in conjunction with FIGS. 2-5, receives the polymer/drug solution (i.e., with or without solvent(s)) via the tubing 130a and the solvent via the tubing 130b. In addition, the nozzle assembly 140 receives high-pressure air from the atomizer 160. During a stent coating application process, the nozzle assembly 140 dispenses, via the nozzle tip 145, the polymer/drug solution and the solvent, which combines in situ, onto the stent 10. In other words, a pure solvent (e.g., about 90% to about 100% polymer and drug free) blends with the coating composition (i.e., polymer and/or drug composition with or without a solvent) out from the nozzle tip 145 before contacting the stent 10. It should be noted, therefore, that the coating composition should be formulated to compensate for the blending of the pure solvent with the composition. During the dispensing, high-pressure air from the atomizer 160 atomizes the combined polymer/drug solution and solvent, leading to a more uniform distribution on the stent 10.

It will be appreciated that the multiple control devices, i.e., the pump controls 110a and 110b, atomizer control 150, and mandrel control 185 can be combined into a single control device to simplify setting parameters for an operator.

Figure 2:
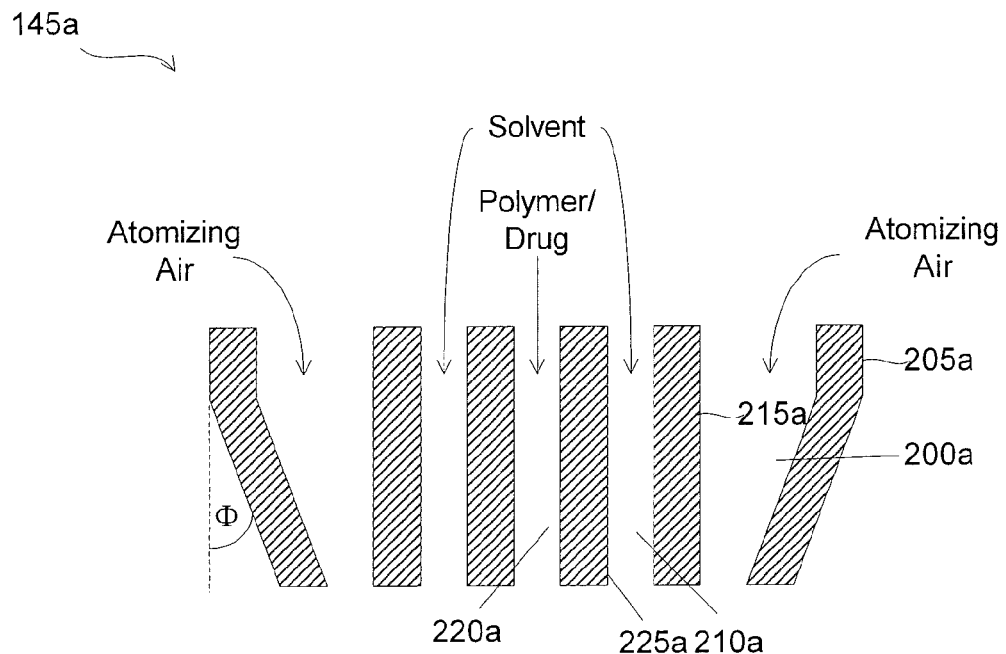
FIG. 2 is a cross section illustrating the nozzle tip of the coating system of FIG. 1 in accordance with an embodiment of the invention.

FIG. 2 is a cross section illustrating a nozzle tip 145a of the coating system 100 (FIG. 1) in accordance with an embodiment of the invention. The nozzle tip 145a includes an atomizing air conduit 200a; a solvent feed conduit 210a; and a polymer/drug feed conduit 220a. In an embodiment of the invention, the air conduit 200a, the solvent feed conduit 210a, and the polymer/drug feed conduit 220a are concentrically positioned tubes, hypotubes, or syringes that run parallel to each other. The atomizing air conduit 200a is in communication with the atomizer 160 via the tubing 170 from which it receives atomizing air. The air conduit 200a circumscribes the solvent feed conduit 210a, which circumscribes the polymer/drug feed conduit 220a, and expels the atomizing air during a coating process so as to atomize the solvent and the polymer/drug expelled from the solvent feed conduit 210a and polymer/drug feed conduit 220a respectively. It will be appreciated by one of ordinary skill in the art that the polymer/drug feed conduit 220a can circumscribe the solvent feed conduit 210a instead of vice versa.

A tube 205a of the air conduit 200a has an inner diameter $d_{1i}$ of about 0.0225 to about 0.45 inches and an outer diameter $d_{1o}$ of about 0.0275 to about 0.50 inches (at the segment of the tube that is not bent). The tube 205a of the air conduit 200a is bent inwards to form an acute angle $\Phi$ of about 0 to about 60 degrees relative to a tube 215a of the solvent feed conduit 210a so as to bias the velocity of the exiting atomizing air towards the dispensed solvent and polymer/drug solution.

Figure 6:
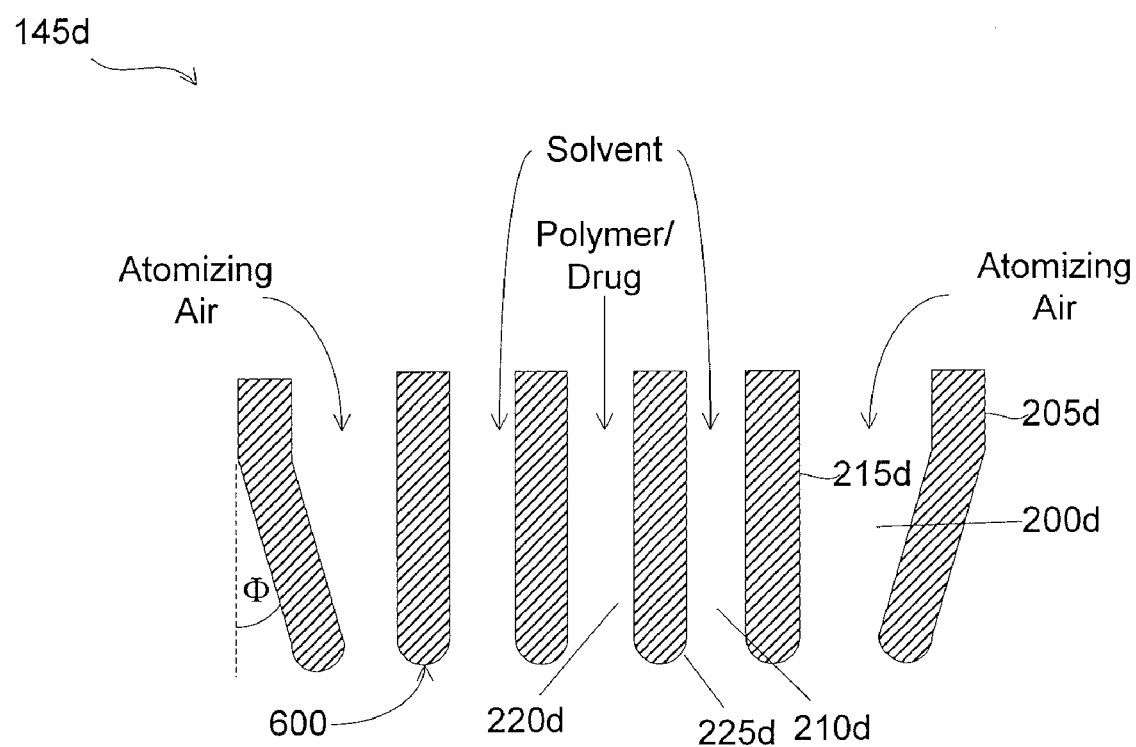
FIG. 6 is a cross section illustrating a nozzle tip according to a fourth embodiment of the invention.

The tube 215a of the solvent feed conduit 210a has an inner diameter $d_{2o}$ of about 0.0125 to about 0.20 inches and an outer diameter $d_{21}$ of about 0.0175 to about 0.25 inches and dispenses pure solvent. The solvent acts to prevent clogging of the polymer/drug feed conduit 220a by preventing accumulation of polymer and/or drugs on a tube 225a of the polymer/drug feed conduit 220a. The solvent mixes in situ with the dispensed polymer/drug when it is ejected out from the nozzle tip 145a. Since only a pure solvent is ejected from the solvent feed conduit 210a, the size of this conduit can be smaller than the size of the polymer/drug conduit 220a, which should be sized to allow for the ejection of a more viscous polymer and/or drug composition. In an embodiment of the invention, the tube 225a, as well as the tubes 205a and 215a, can each have an arcuate end, such as end 600 as shown in FIG. 6, to further prevent accumulation of polymer that may cause blockage. In addition, the tubes 205a, 215a, and 225a can be made of or coated with a non-stick material (e.g., TEFLON) to prevent accumulation of the polymer, which can lead to blockage.

The polymer/drug feed conduit 220a dispenses a polymer and/or drug from the polymer/drug reservoir 125a received via the tubing 130a. In an embodiment of the invention, the tube 225a of the polymer/drug feed conduit 220a has an inner diameter $d_{31}$ of about 0.0025 to about 0.05 inches and an outer diameter $d_{30}$ of about 0.0075 to about 0.10 inches.

Figure 3:
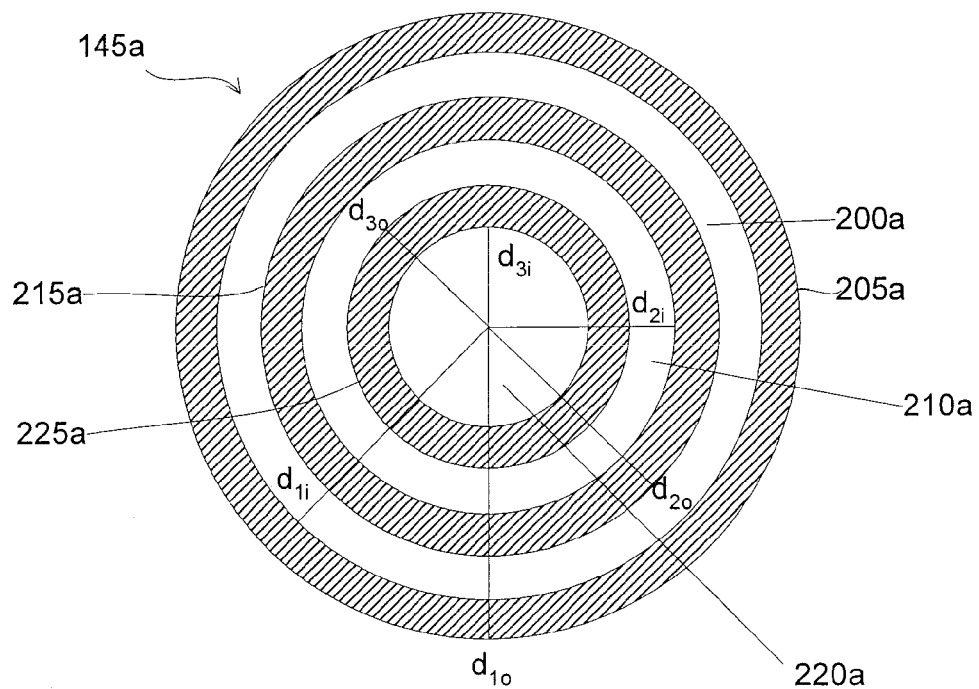
FIG. 3 is a bottom view of the nozzle tip of the nozzle tip of FIG. 1.

FIG. 3 is a bottom view of the nozzle tip of the nozzle tip 145a. The polymer/drug feed conduit 220a is centered with the nozzle tip 145a. The solvent feed conduit 210a circumscribes the polymer/drug feed conduit 220a. The atomizing air conduit 200a circumscribes the solvent feed conduit 210a.

Figure 4:
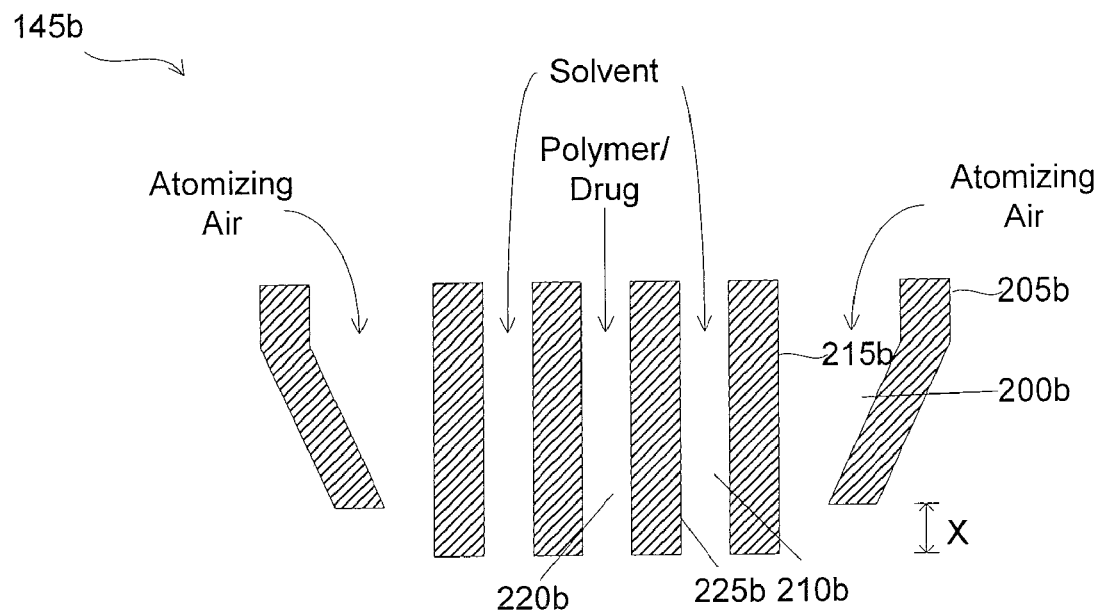
FIG. 4 is a cross section illustrating a nozzle tip according to a second embodiment of the invention.

FIG. 4 is a cross section illustrating a nozzle tip 145b according to another embodiment of the invention. The nozzle tip 145b is substantially similar to the nozzle tip 145a and includes the same components. However, the tube 205b of the air conduit 200b does not extend to the same length as the tube 215b of the solvent feed conduit 210b, i.e., the air conduit tube 205b is shorter than the solvent feed conduit tube 215b by a distance X of, for example, up to about 0.2 inches. This nozzle tip 145b geometry substantially prevents any polymer clumping within the air conduit 200b since the tubes 215b and 225b extend out from the tube 205b.

Figure 5:
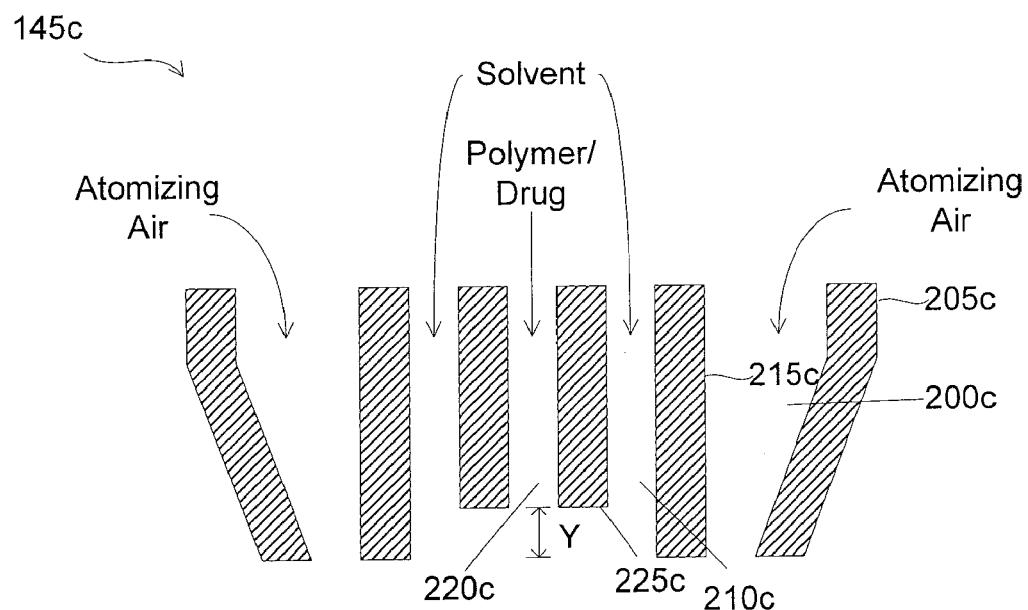
FIG. 5 is a cross section illustrating a nozzle tip according to a third embodiment of the invention.
Figure 5A:
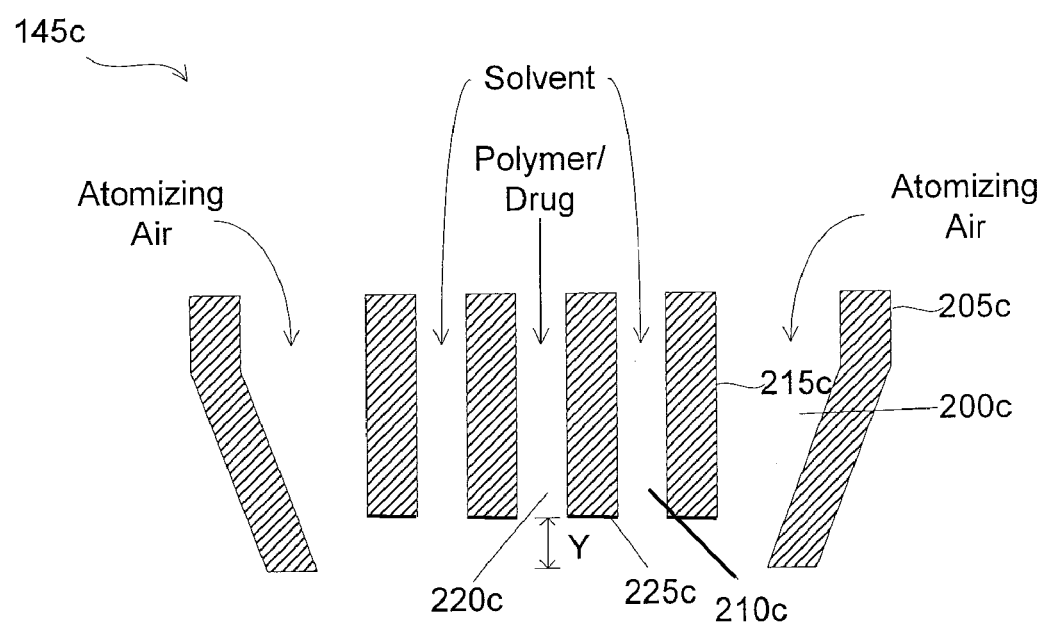
FIG. 5A is a cross section illustrating a nozzle tip according to another embodiment of the invention.

FIG. 5 is cross section illustrating a nozzle tip 145c according to another embodiment of the invention. The nozzle tip 145c is substantially similar to the nozzle tip 145a and includes the same components. However, the polymer/drug feed conduit tube 225c is shorter than the solvent feed conduit tube 215c that circumscribes it, i.e., the polymer/drug feed conduit 220c is recessed within the solvent feed conduit 210c by a distance Y of, for example, up to about 0.2 inches. This nozzle tip 145c geometry substantially prevents any polymer clumping within the air conduit 200c and also ensures that the bottom of the tube 225c is swept clean with solvent from the solvent feed conduit 210c. It should also be noted that the tube 215c can also be recessed in the same extent as the tube 225c as shown in FIG. 5A or be positioned such that the bottom of the tube 215c is between the bottom of the tubes 205c and 225c.

FIG. 6 is cross section illustrating a nozzle tip 145*d* according to a fourth embodiment of the invention. The nozzle tip 145*d* is substantially similar to the nozzle tip 145*a* and includes the same components. However, each of the tubes 205*d*, 215*d*, and 225*d* have arcuate ends, such as arcuate end 600. The arcuate ends of the tubes 205*d*, 215*d*, and 225*d* enable the solvent to contact more of the tubes' surface area, thereby prevent accumulation of the polymer on the tubes 205*d*, 215*d*, and 225*d*, which may lead to clogging of the nozzle tip 145*d*.

While particular embodiments of the present invention have been shown and described, it will be obvious to those skilled in the art that changes and modifications can be made without departing from this invention in its broader aspects. For example, the nozzle tip 145 can use internal mixing in place of external mixing. Therefore, the appended claims are to encompass within their scope all such changes and modifications as fall within the true spirit and scope of this invention.

What is claimed is:

1. A nozzle assembly to dispense a solvent and a polymer onto a stent, comprising:
   a first tube adjacent a stent, the first tube adapted to deliver a composition including a polymer to the stent;
   a second tube disposed over the first tube and adapted to deliver a solvent, the second tube further adapted to blend or mix the solvent with the composition when the composition and the solvent are discharged out from the first tube and the second tube toward the stent, respectively; and
   a third tube disposed over the second tube and adapted to atomize the composition and the solvent that are discharged toward the stent,
   wherein the second tube is positioned relative to the first tube so that when the solvent is discharged from the second tube, the solvent cleans the composition off the tip of the first tube.

2. The nozzle assembly of claim 1, wherein the nozzle assembly enables external atomization and mixing of the solvent and polymer.

3. The nozzle assembly of claim 1, wherein the composition further includes a drug.

4. The nozzle assembly of claim 1, wherein an end of the third tube is bent towards the second tube.

5. The nozzle assembly of claim 1, wherein the first or second tube protrudes out from the third tube.

6. The nozzle assembly of claim 1, wherein the first tube is recessed within the second tube.

7. The nozzle assembly of claim 1, wherein the tubes are made of or coated with a non-stick material.

8. The nozzle assembly of claim 1, wherein the tubes have arcuate ends.

9. The nozzle assembly of claim 1, wherein the second tube has an annular aperture for discharging the polymer and that circumscribes the first tube, and the third tube has an annular aperture for discharging a gas and that circumscribes the second tube.

10. The nozzle assembly of claim 1, wherein the second tube is positioned relative to the first tube so that when the solvent is discharged from the second tube and the composition is discharged from the first tube, the solvent at least partially dissolves the discharged composition before the discharged composition contacts the stent.

11. The nozzle assembly of claim 1, wherein the stent and first tube are movable relative to each other.

* * * * *